United States Patent
Garabedian et al.

(10) Patent No.: US 6,866,660 B2
(45) Date of Patent: Mar. 15, 2005

(54) INTRAVASCULAR CATHETER WITH COMPOSITE REINFORCEMENT

(75) Inventors: Robert J. Garabedian, West Townsend, MA (US); John Griego, Blackstone, MA (US); Earl Bardsley, Newton, MA (US); Dean A. Schaefer, Roslindale, MA (US); Cang D. Dao, Foxboro, MA (US); Steven M. Anderson, Shrewsbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/339,055

(22) Filed: Jan. 9, 2003

(65) Prior Publication Data

US 2003/0097119 A1 May 22, 2003

Related U.S. Application Data

(63) Continuation of application No. 09/684,819, filed on Oct. 10, 2000, now Pat. No. 6,508,805, which is a continuation of application No. 09/234,203, filed on Jan. 20, 1999, now Pat. No. 6,171,295.

(51) Int. Cl.$^7$ .............................................. A61M 25/00
(52) U.S. Cl. ....................... 604/527; 604/524; 138/123; 138/172
(58) Field of Search ................................ 604/523–532, 604/264; 138/118, 123, 124, 125, 126, 127, 129, 130, 140, 141, 143, 144, 172, 114

(56) References Cited

U.S. PATENT DOCUMENTS

| | | | |
|---|---|---|---|
| 3,416,316 A | 12/1968 | Edwards | |
| 3,592,238 A * | 7/1971 | Scheffler et al. | ............ 138/114 |
| 3,605,750 A | 9/1971 | Sheridan et al. | |
| 3,618,609 A | 11/1971 | Glick | |
| 4,063,561 A | 12/1977 | McKenna | |
| 4,257,421 A * | 3/1981 | Beal | ....................... 604/170.01 |
| 4,279,252 A | 7/1981 | Martin | |
| 4,385,635 A | 5/1983 | Ruiz | |
| 4,425,919 A | 1/1984 | Alston, Jr. et al. | |
| 4,430,083 A | 2/1984 | Ganz et al. | |
| 4,444,186 A | 4/1984 | Wolvek et al. | |
| 4,464,176 A | 8/1984 | Wijayarathna | |
| 4,469,483 A | 9/1984 | Becker et al. | |
| 4,563,181 A | 1/1986 | Wijayarathna et al. | |
| 4,571,240 A | 2/1986 | Samson et al. | |
| 4,596,563 A | 6/1986 | Pande | |
| 4,636,346 A | 1/1987 | Gold et al. | |
| 4,657,024 A | 4/1987 | Coneys | |
| 4,665,604 A | 5/1987 | Dubowik | |
| 4,690,175 A | 9/1987 | Ouchi et al. | |
| 4,753,765 A | 6/1988 | Pande | |
| 4,764,324 A | 8/1988 | Burnham | |
| 4,817,613 A | 4/1989 | Jaraczewski et al. | |

(List continued on next page.)

Primary Examiner—Nicholas D. Lucchesi
Assistant Examiner—Jennifer J Maynard
(74) Attorney, Agent, or Firm—Crompton, Seager & Tufte, LLC

(57) ABSTRACT

An intravascular catheter that exhibits the combined features of superior flexibility, softness, radiopacity and oval/kink resistance. The catheter includes an elongate shaft having a proximal region, a distal region and a lumen extending therethrough. The proximal region of the shaft includes an inner lubricious polymer layer, a reinforcement layer and an outer layer. The reinforcement layer comprises a braid having one or more metallic members and a plurality of polymer members wherein each polymer member comprises a plurality of monofilaments, preferably formed of LCP. The polymer members of the braid provide improved flexibility and softness in addition to high burst pressure. The metallic member(s) of the braid provide improved radiopacity and oval/kink resistance. The catheter may also include a longitudinal member extending along the reinforcement layer.

20 Claims, 2 Drawing Sheets

U.S. PATENT DOCUMENTS

| | | |
|---|---|---|
| 4,838,879 A | 6/1989 | Tanabe et al. |
| 4,842,590 A | 6/1989 | Tanabe et al. |
| 4,863,442 A | 9/1989 | DeMello et al. |
| 4,886,506 A | 12/1989 | Lovgren et al. |
| 4,898,591 A | 2/1990 | Jang et al. |
| 4,899,787 A | 2/1990 | Ouchi et al. |
| 4,904,431 A | 2/1990 | O'Maleki |
| 4,925,710 A | 5/1990 | Buck et al. |
| 4,963,306 A | 10/1990 | Weldon |
| 4,990,143 A | 2/1991 | Sheridan |
| 5,019,057 A | 5/1991 | Truckai |
| 5,037,404 A | 8/1991 | Gold et al. |
| 5,045,072 A | 9/1991 | Castillo et al. |
| 5,057,092 A | 10/1991 | Webster, Jr. |
| 5,061,257 A | 10/1991 | Martinez et al. |
| 5,069,674 A | 12/1991 | Fearnot et al. |
| 5,078,702 A | 1/1992 | Pomeranz |
| 5,088,991 A | 2/1992 | Weldon |
| 5,156,785 A | 10/1992 | Zdrahala |
| 5,171,232 A | 12/1992 | Castillo et al. |
| 5,176,660 A | 1/1993 | Truckai |
| 5,201,723 A | 4/1993 | Quinn |
| 5,221,270 A | 6/1993 | Parker |
| 5,234,416 A | 8/1993 | Macaulay et al. |
| 5,248,305 A | 9/1993 | Zdrahala |
| 5,254,107 A | 10/1993 | Soltesz |
| 5,290,230 A | 3/1994 | Ainsworth et al. |
| 5,300,048 A | 4/1994 | Drewes, Jr. et al. |
| 5,318,032 A | 6/1994 | Lonsbury et al. |
| 5,335,410 A | 8/1994 | Burnham |
| 5,370,691 A | 12/1994 | Samson |
| 5,380,304 A | 1/1995 | Parker |
| 5,399,164 A | 3/1995 | Snoke et al. |
| 5,403,292 A | 4/1995 | Ju |
| 5,423,773 A * | 6/1995 | Jimenez .................. 604/526 |
| 5,433,713 A | 7/1995 | Trotta |
| 5,441,489 A | 8/1995 | Utsumi et al. |
| 5,445,624 A | 8/1995 | Jimenez |
| 5,451,209 A | 9/1995 | Ainsworth et al. |
| 5,454,795 A | 10/1995 | Samson |
| 5,499,973 A | 3/1996 | Saab |
| 5,509,910 A | 4/1996 | Lunn |
| 5,533,987 A | 7/1996 | Pray et al. |
| 5,538,510 A | 7/1996 | Fontirroche et al. |
| 5,540,707 A | 7/1996 | Ressemann et al. |
| 5,542,924 A | 8/1996 | Snoke et al. |
| 5,545,149 A | 8/1996 | Brin et al. |
| 5,582,619 A | 12/1996 | Ken |
| 5,584,821 A | 12/1996 | Hobbs et al. |
| 5,601,538 A | 2/1997 | Deem |
| 5,603,705 A | 2/1997 | Berg |
| 5,622,665 A | 4/1997 | Wang |
| 5,624,461 A | 4/1997 | Mariant |
| 5,658,263 A | 8/1997 | Dang et al. |
| 5,674,208 A | 10/1997 | Berg et al. |
| 5,676,659 A | 10/1997 | McGurk |
| 5,690,666 A | 11/1997 | Berenstein et al. |
| 5,702,373 A | 12/1997 | Samson |
| 5,718,711 A | 2/1998 | Berenstein et al. |
| 5,730,733 A | 3/1998 | Mortier et al. |
| 5,749,891 A | 5/1998 | Ken et al. |
| 5,755,704 A * | 5/1998 | Lunn ..................... 604/527 |
| 5,782,811 A | 7/1998 | Samson et al. |
| 5,817,057 A | 10/1998 | Berenstein et al. |
| 5,826,587 A | 10/1998 | Berenstein et al. |
| 5,827,201 A | 10/1998 | Samson et al. |
| 5,833,652 A | 11/1998 | Preissman et al. |
| 5,833,705 A | 11/1998 | Ken et al. |
| 5,853,418 A | 12/1998 | Ken et al. |
| 5,891,112 A | 4/1999 | Samson |
| 5,891,114 A | 4/1999 | Chien et al. |
| 5,895,391 A | 4/1999 | Farnholtz |
| 5,899,892 A | 5/1999 | Mortier et al. |
| 5,927,345 A | 7/1999 | Samson |
| 5,947,940 A | 9/1999 | Beisel |
| 6,004,338 A | 12/1999 | Ken et al. |
| 6,090,072 A | 7/2000 | Kratoska et al. |
| 6,171,295 B1 | 1/2001 | Garabedian et al. |
| 6,197,014 B1 | 3/2001 | Samson et al. |
| 6,290,692 B1 | 9/2001 | Klima et al. |
| 6,368,316 B1 | 4/2002 | Jansen et al. |
| 6,508,805 B1 | 1/2003 | Garabedian et al. |

\* cited by examiner

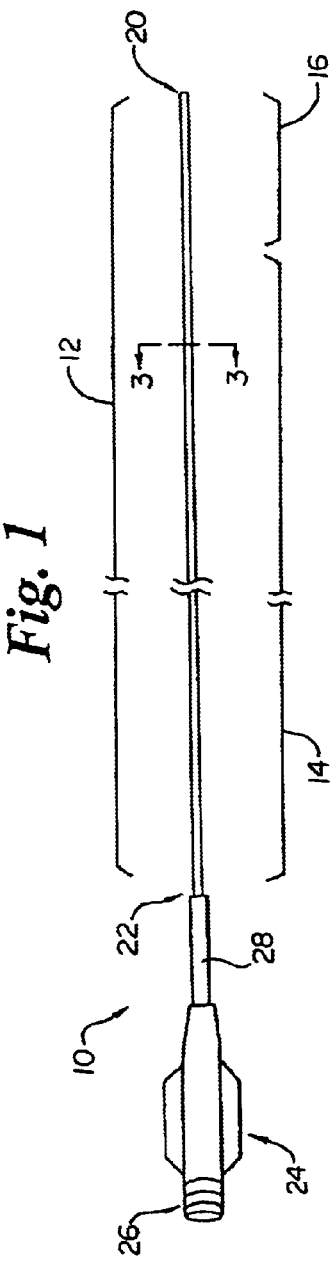
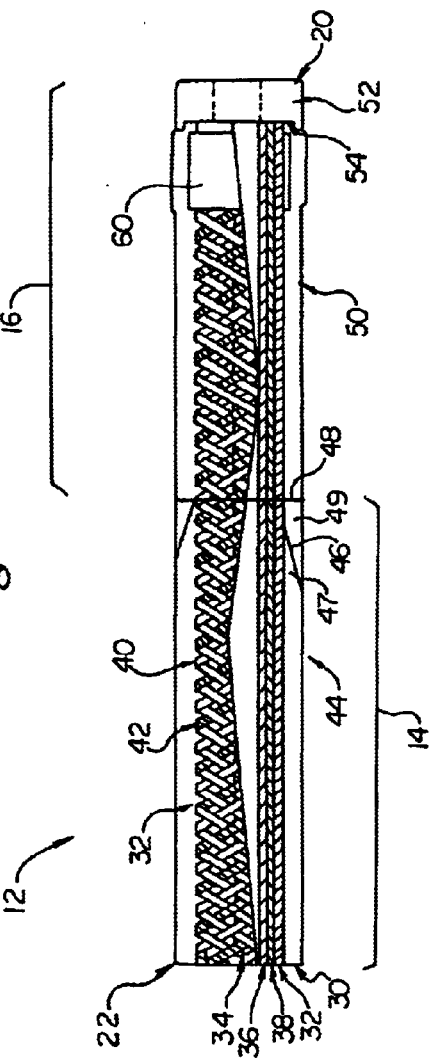

INTRAVASCULAR CATHETER WITH COMPOSITE REINFORCEMENT

This application is a continuation of U.S. patent application Ser. No. 09/684,819, filed Oct. 10, 2000 now U.S. Pat. No. 6,508,805; which is a continuation of U.S. patent application Ser. No. 09/234,203, filed Jan. 20, 1999, now U.S. Pat. No. 6,171,295.

BACKGROUND OF THE INVENTION

The present invention generally relates to intravascular devices. More specifically, the present invention relates to reinforced intravascular catheters.

Intravascular catheters are used in a wide variety of relatively non-invasive medical procedures. Such intravascular catheters may be used for diagnostic or therapeutic purposes. Generally, an intravascular catheter allows a physician to remotely perform a medical procedure by inserting the catheter into the vascular system of the patient at a location that is easily accessible and thereafter navigating the catheter to the desired target site. By this method, virtually any target site in the patient's vascular system may be remotely accessed, including the coronary, cerebral, and peripheral vasculature.

The distance between the access site and the target site is often in excess of 100 cm. The inside diameter of the vasculature at the access site is often less than 2 cm, and the inside diameter of the vasculature at the target site is often less than 0.5 cm. Accordingly, intravascular catheters must be relatively long and thin. Furthermore, in order to navigate through the patient's tortuous vascular system, intravascular catheters must be very flexible. It is also desirable that intravascular catheters be relatively soft in order to minimize the probability of damaging vascular tissue.

Intravascular catheters typically have a radiopaque portion and are guided through the patient's vascular system with the assistance of x-ray fluoroscopy. In this manner, a physician may manipulate the proximal end of the catheter and fluoroscopically monitor the corresponding movement of the distal end of the catheter. As such, it is desirable that intravascular catheters be sufficiently radiopaque along their length and particularly at their distal end such that the physician is able to clearly monitor the progress of the catheter as it is being advanced from the vascular access site to the vascular target site.

After the intravascular catheter has been navigated through the patient's vascular system with the distal end thereof adjacent the target site, the catheter may be used for various diagnostic and/or therapeutic purposes. Frequently, diagnostic and therapeutic techniques require the infusion of fluids through the catheter. For example, it may be desirable to inject radiopaque contrast media through the catheter to provide enhanced fluoroscopic visualization for diagnostic purposes, or to inject pharmaceutical solutions (i.e., drugs) to the target site for therapeutic purposes. In order to maintain a fluid path, it is desirable that intravascular catheters be sufficiently resistant to kinking. In addition, because such fluids are delivered under pressure, it is also desirable that intravascular catheters be sufficiently resistant to bursting.

To satisfy some of these desirable features, prior art intravascular catheters have utilized a reinforcement structure such as a braid or coil disposed between an inner lubricious tubular layer and an outer flexible tubular layer. A braid reinforcement stricture offers high resistance to bursting and improves the connection integrity between individual shaft segments. However, braid reinforcement offers limited resistance to ovaling, which is a precursor to kinking. A coil reinforcement structure, by contrast, provides adequate resistance to ovaling and kinking, but does not sufficiently enhance the connection integrity between individual shaft segments.

SUMMARY OF THE INVENTION

The present invention overcomes these disadvantages by providing an intravascular catheter that exhibits the combined features of superior flexibility, softness, radiopacity, durability, high burst strength, and oval/kink resistance.

An intravascular catheter in accordance with one embodiment of the present invention includes an elongate shaft having a proximal region, a distal region and a lumen extending therethrough. The proximal region of the shaft includes an inner lubricious polymer layer, a reinforcement layer and an outer layer. The reinforcement layer comprises a braid having at least one metallic member and a plurality of polymer members wherein each polymer member comprises a plurality of monofilaments. The monofilaments may be made of LCP having a substantially circular cross-section and may be unfused or fused together. The monofilaments may be arranged side-by-side to collectively define a flat cable that may be twisted along the length of the shaft. The metallic member(s) may be made of a highly radiopaque material. The catheter may further include a longitudinal member extending along the reinforcement layer. The longitudinal member may also comprise a plurality of longitudinal monofilaments made of a polymer, such as LCP. The distal region of the shaft may include a radiopaque marker band surrounding the reinforcement layer and an atraumatic tip layer surrounding a portion of the radiopaque marker band and a portion of the reinforcement layer. The tip layer may extend distally beyond the distal ends of the inner layer and the reinforcement layer to form an atraumatic soft distal tip.

The brand reinforcement provides high burst strength and durability. The polymer members of the braid provide enhanced flexibility and softness, and the metallic members (s) of the braid provide enhanced radiopacity and resistance to ovaling and kinking. These combined features are not found in the prior art.

An intravascular catheter in accordance with another embodiment of the present invention includes an elongate shaft having a proximal region, a distal region and a lumen extending therethrough. The proximal region of the shaft includes an inner lubricious polymer layer, a reinforcement layer and an outer layer. The outer layer includes a proximal portion made of a first material having a first durometer, and a distal portion made of a second material having a second durometer less than the first durometer. The reinforcement layer comprises a braid having one or more metallic members and a plurality of polymer members wherein each polymer member comprises a plurality of monofilaments. The distal region of the shaft includes a radiopaque marker band surrounding the reinforcement layer and an atraumatic tip layer surrounding the radiopaque marker band and the reinforcement layer. The tip layer is made of a third material having a third durometer less than the second durometer. The tip layer includes a distal portion that extends beyond the distal ends of the inner layer and the reinforcement layer to form an atraumatic soft distal tip.

BRIEF DESCRIPTION OF THE DRAWINGS

FIG. 1 is a plan view of an intravascular catheter in accordance with the present invention;

FIG. 2 is a partially sectioned detailed view of the elongate shaft of the intravascular catheter illustrated in FIG. 1. Specifically, the outer layer has been removed on the top portion of the shaft to expose the reinforcement layer and the radiopaque marker band. In addition, the bottom portion has been sectioned to expose the various layers of the shaft;

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 3:
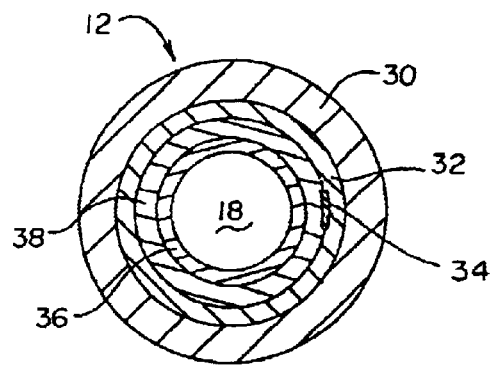
FIG. 3 is a cross-sectional view taken along line 3—3 in FIG. 1.

FIG. 1 illustrates intravascular catheter 10 in accordance with the present invention. Catheter 10 includes an elongate shaft 12 having a proximal region 14 and a distal region 16. The catheter 10 includes a lumen 18 (as best seen in FIG. 3) extending through the entire length of the elongate shaft 12 to an opening at the distal end 20 of the shaft 12. Catheter 10 may have a length of 80 to 150 cm and an outside diameter of approximately 3 F.

A manifold 24 is connected to the proximal end 22 of the shaft 12 which includes an interior (not visible) in fluid communication with the lumen 18 of the elongate shaft 12. Manifold 24 includes a standard fitting 26 for connection to a fluid source such as a syringe. A strain relief 28 is disposed between the manifold 24 and the proximal end 22 of the shaft 12 in order to reduce the tendency of the shaft to kink therebetween. The proximal end 22 of the elongate shaft 12 may extend through the strain relief 28 for connection to the manifold 24. Alternatively, the distal end of the strain relief 28 may be connected to the proximal end 22 of the elongate shaft 12 with the proximal end of the strain relief 12 connected to the manifold 24.

With either arrangement, the intravascular catheter 10 provides a fluid path from the fitting 26 of the manifold 24 to the distal end 20 of the elongate shaft 12 by way of the interior (not visible) of the manifold 24 and the lumen 18 of the elongate shaft 12. This intravascular catheter 10 may be advanced over a guide wire and used to deliver diagnostic and/or therapeutic fluids to a desired vascular target site using conventional techniques.

FIG. 2 is a partially sectioned detailed view of the elongate shaft 12 of the intravascular catheter 10 illustrated in FIG. 1. On the top portion of the shaft 12, the outer layer 30 has been removed to expose the reinforcement layer 32 and the longitudinal member 34. On the bottom portion, the shaft 12 has been sectioned to illustrate the various layers 30, 32, 36, and 38 of the shaft 12.

Elongate shaft 12 includes a proximal region 14 and a distal region 16. Both the proximal region 14 and a portion of the distal region 16 include an inner lubricious polymer layer 36 surrounded by a reinforcement layer 32 which, in turn, is surrounded by an outer layer 30. The outer layer 30 may be loaded with a radiopaque contrast material such as barium sulfate, preferably loaded at 30% by weight. A tie layer 38 may be provided between the reinforcement layer 32 and the inner lubricious layer 36. Each of these layers are most clearly illustrated on the bottom portion of the shaft 12 shown in FIG. 2 and the cross-sectional view taken along line 3-3 as shown in FIG. 3.

Inner layer 36 is formed of a lubricious polymer such as PTFE or HDPE and preferably has a relatively thin wall to minimize profile. Inner layer 36 has an inside diameter sufficiently large to accommodate a conventional guidewire and to accommodate the delivery of fluids therethrough at a sufficient flow rate. For example, the inside diameter of the inner layer 36 may be approximately 0.027 inches and the wall thickness of the inner layer 36 may be approximately 0.0005 inches. The inner layer 36 may be formed, for example, by coating or extruding a lubricious polymer such as PTFE over a removable mandrel, or by using other known manufacturing techniques.

As mentioned previously, a tie layer 38 may be utilized to secure the reinforcement layer 32 to the inner lubricious layer 36. Tie layer 38 enhances the bond between the inner lubricious layer 36, the reinforcement layer 32, and the outer layer 30. Tie layer 38 also fills any micro-pores that may form in the inner layer 36 to thereby increase burst strength. Further, tie layer 38 maintains the position of the reinforcement layer 32 on the inner layer 36 during the manufacturing process. The thickness of the tie layer 38 may be approximately 0.0003 inches to reduce the corresponding increase in profile. An example of a suitable material for tie layer 38 is polyurethane, which may be coated onto the inner lubricious layer 36.

Reinforcement layer 32 comprises a plurality of braided polymer members 40 and one or more metallic members 42. For example, the reinforcement layer 32 in the form of a braid having a total of eight members may comprise six polymer members 40 and two metallic members 42. Those skilled in the art will recognize that the braid reinforcement layer 32 may vary in pattern, strand quantity, pick-count, etc., without departing from the scope of the present invention.

Figure 5A:
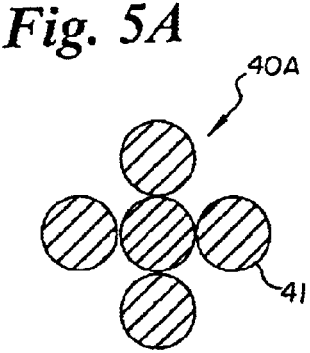
FIGS. 5A and 5B are cross-sectional views of the polymer member of the reinforcement layer illustrated in FIGS. 2–4.
Figure 5B:
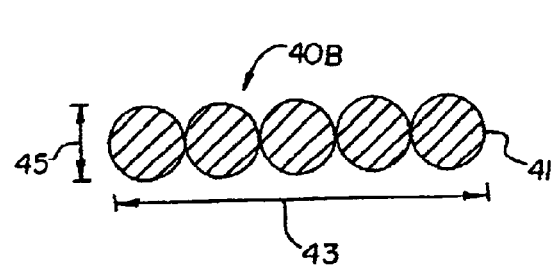

Each polymer member 40 comprises a plurality of monofilaments 41 to collectively define a cable 40A or 40B, illustrated in FIGS. 5A and 5B, respectively. FIGS. 5A and 5B show cross-sectional views of the polymer cables 40A and 40B of the reinforcement layer. FIG. 5A illustrates a round cable 40A, and FIG. 5B illustrates a flat cable 40B.

The monofilaments 41 may be unfused or fused together depending on the desired characteristics. If the monofilaments 41 are fused together, the polymer member 40 has mechanical characteristics similar to that of a solid rod. If the monofilaments 41 are not fused together, the polymer member 40 has mechanical characteristics similar to that of a cable. A cable, as opposed to a solid rod, is more flexible and is able to withstand more fatigue due to repeated bending. As such, a reinforcement layer 32 utilizing braided polymer members 40 comprising a plurality of unfused monofilaments 41 provide a shaft 12 that is more flexible and more durable. These features are significant because the catheter 10 must be able to navigate tortuous vasculature and withstand harsh handling conditions.

The monofilaments 41 may be made of a liquid crystal polymer (LCP) available under the trade name VECTRAN. Each monofilament may have a circular cross-section having a diameter of 0.0007 inches. Each polymer member 40 may comprise two (2) to ten (10), and preferably five (5) monofilaments 41 which, as stated previously, may be fused or unfused. If the monofilaments 41 are unfused, the monofilaments of the polymer member 40 are typically arranged side-by-side to essentially define a flat cable 40B as shown in FIG. 5B. It is possible, however, that the monofilaments be arranged in any manner to collectively define a flat cable 40B, a round cable 40A, or any other desired geometry.

Furthermore, if the monofilaments are arranged to collectively define a flat cable 40B, the flat cable 40B may be twisted along the length of the catheter shaft 12. Specifically, the flat cable 40B has a pair of major sides 43 and a pair of minor sides 45. Each of the major sides 43 faces the lumen 18 at various points along the length of the shaft 12. The flat cable may have random twists or a twist every 7.5 inches, depending on manufacturing conditions. Twisting the flat cable 40B may provide the advantage of improved guide wire movement due to ridges formed on the inside surface of the inner layer 36.

The metallic member 42 may be formed of stainless steel or a highly radiopaque material such as gold, tungsten, iridium, or an alloy thereof. If a plurality of metallic members 42 are utilized, one or more of the metallic members 42 may comprise stainless steel to provide superior strength and one or more metallic members 42 may comprise a highly radiopaque material to provide enhanced radiopacity. Although stainless steel provides higher radiopacity relative to most polymers, a more dense material such as those identified above are preferred for purposes of radiographic visualization. The metallic members 42 may have a rectangular cross-section or a circular cross-section, depending on the desired mechanical characteristics. Metallic member 42 may have a circular cross-section with a diameter of approximately 0.0016 inches to minimize profile.

Longitudinal member 34 is disposed between the reinforcement layer 32 and the tie layer 38 to provide enhanced resistance to elongation as the catheter 10 is removed from the patient's body. Longitudinal member 34 may be an LCP flat cable, similar to cable 40B.

When the polymer members 40 and the metallic member(s) 42 are braided, the reinforcement layer 32 provides superior flexibility and softness by virtue of the polymer members 40 in addition to superior radiopacity and kink resistance by virtue of the metallic member(s) 42. These combined features are not found in prior art intravascular devices.

The proximal region 14 of shaft 12 includes an outer layer 30 formed by interrupted layer coextrusion (ILC) as described in U.S. Pat. No. 5,622,665 to Wang, which is hereby incorporated by reference. The ILC portion 44 of outer layer 30 includes a proximal portion 47 formed of a relatively high durometer polymer and a distal portion 49 formed of a relatively low durometer polymer. By virtue of the ILC process, the proximal region 14 gradually transitions from the relatively high durometer polymer 47 to the relatively low durometer polymer 49. The transition between the relatively high durometer polymer 47 to the relatively low durometer polymer 49 is graphically illustrated by transition line 46. However, transition line 46 is typically not visible due to the intermixing of polymers during the ILC process. The ILC portion 44 may be formed of a suitable polymer such as polyether block amide having a wall thickness of approximately 0.0025 inches. For example, the proximal ILC portion 47 may be formed of PEBAX™ 7233, which has a durometer of 72D and the distal ILC portion 49 may be formed of PEBAX™ 3533 having a durometer of 35D.

The proximal region 14 of the outer layer 30 abuts the distal region 16 of the outer layer 30 at junction line 48. The distal region 16 of the shaft 12 includes a proximal portion 50 and a distal portion 52. Both the proximal portion 50 and the distal portion 52 of the distal region 16 may be formed of the same or different polymers which have a durometer less than the durometer of the distal portion 49 of the ILC section 44. The distal portion 52 of the distal region 16 may have the same or lower durometer than the durometer of the proximal portion 50. The proximal portion 50 and the distal portion 52 may be formed of a polyether block amide polymer such as PEBAX™ 2533 having a durometer of 25D. The proximal portion 50 encapsulates the radiopaque marker band 60.

Radiopaque marker band 60 may be formed of gold, tungsten, iridium, or an alloy thereof. The radiopaque marker band 60 is disposed over the reinforcement layer 32 and may optionally be swaged onto the reinforcement layer 32. The radiopaque marker band 60 may optionally be adhesively secured to the reinforcement layer 32 or held in place by the encapsulating proximal portion 50.

The distal portion 52 of the distal region 16 abuts the distal ends of the various layers 36, 38, and 32 and forms a lap joint with proximal portion 50 along junction line 54. Junction line 54 between the proximal portion 50 of the outer layer 30 and the distal portion 52 is not present if the proximal portion 50 and the distal portion 52 are made of the same material, i.e., the proximal portion 50 and the distal portion 52 form a single unitary piece. Encapsulated marker band 60 may have a length of approximately 1.0 mm and may be positioned approximately 0.5 to 1.5 mm proximal of the distal end of the shaft 12. Distal portion 52 may extend approximately 0.5 to 1.0 mm beyond the distal end of the inner layer 36, tie layer 38 and reinforcement layer 32 to form an atraumatic soft tip.

Figure 4:
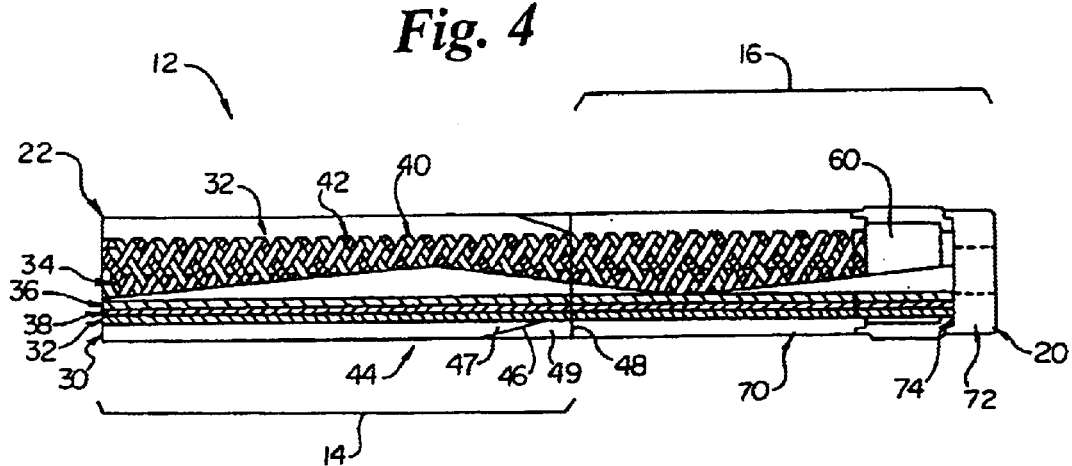
FIG. 4 is an alternative embodiment of the shaft illustrated in FIG. 2.

FIG. 4 is an alternate embodiment of the elongate shaft 12 illustrated in FIG. 2. Specifically, FIG. 4 illustrates an alternative arrangement of the outer layer 30 of the distal region 16 of the elongate shaft 12. Except as described herein, all aspects of the embodiment illustrated in FIG. 4 are the same as those described with reference to the embodiment illustrated in FIG. 2.

Distal region 16 includes a proximal portion 70 and a distal portion 72. Proximal portion 70 and distal portion 72 may be formed of the same materials as proximal portion 50 and distal portion 52, respectively, as described with reference to FIG. 2. Distal portion 72 encapsulates the outer surface and distal face of the marker band 60. Distal portion 72 and proximal portion 70 are connected by a lap joint as defined by junction line 74. Junction line 74 between the proximal portion 70 and the distal portion 72 is not present if the proximal portion 70 and the distal portion 72 are formed of the same or similar materials. Distal portion 72 is approximately 2.5 to 3.0 mm in length and extends approximately 1.0 mm beyond the distal ends of the inner layer 36, the tie layer 38, and the reinforcement layer 32 to form an atraumatic tip.

The elongate shaft 12, including the embodiment illustrated in FIG. 2 and the embodiment illustrated in FIG. 4, may be manufactured by a number of suitable manufacturing processes including the process described hereinafter. The inner layer 36 and the tie layer 38 may be obtained prefabricated from a suitable vendor, such as H.V. Technologies, and provided as discrete tubes or on a spool as a continuous tube. Member 34 is then disposed on the tube of inner layer 36 and tie layer 38. Optionally, the longitudinal member 34 may be applied during the braiding step. The reinforcement layer 32 is then braided over the axial member 34 and the tube of inner layer 36 and tie layer 38. The braided subassembly is subsequently cut to the desired length. The marker band 60 is slid over the reinforcement layer 32 into position adjacent the distal end 20 of the elongate shaft 12. The proximal portion 50, 70 of the distal region 16 is slid over the reinforcement layer 32 adjacent the marker band 60. The proximal region 14 comprising a prefabricated ILC tube 44 is slid over the proximal end 22 of the elongate shaft 12. A heat shrink tube (e.g., FEP) is then placed over the shaft 12 components and the composite subassembly is pulled through a heated die. The die is heated to 380°–430° F. causing the components of the shaft 12 to be fused and compressed together by the combined heat and radial force. The heat shrink tube is then removed, exposing the completed shaft 12 subassembly. The manifold 24 and the strain relief 28 are then attached to the proximal end 22 of the elongate shaft 12 using conventional techniques. The catheter 10 is then tested for minimum performance criteria including burst pressure. The distal end 20 of the elongate shaft 12 is then trimmed to the desired length, and the distal portion 52, 72 of the distal region 16 is thermally fused thereto by, for example, inserting a mandrel into the lumen 18 and heating the tip 20 at 350° F. for twenty-six (26) seconds. A lubricious coating is then applied to exterior of the catheter shaft 12.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An elongate shaft for use in a catheter, the elongate shaft comprising:
   a polymer inner layer defining a lumen;
   a braid member disposed about the inner layer;
   a longitudinal member disposed between the inner layer and the braid member; and
   a polymer outer layer disposed about the braid member;
   wherein the longitudinal member is in the shape of a ribbon having two major faces and two minor faces, wherein the longitudinal member is twisted with respect to the inner layer such that, at a first location along the elongate shaft the first major face is directed towards the inner layer, and at a second location along the elongate shaft the second major face is directed towards the inner layer, forming a twist between the first location and the second location.

2. The elongate shaft of claim 1, wherein the twist creates a ridge along the lumen defined by the inner layer, the ridge reducing the amount of force required to move a guidewire relative to the elongate shaft when the guidewire is advanced or withdrawn within the lumen.

3. The elongate shaft of claim 1, wherein the braid member includes a polymer element and a metal element.

4. The elongate shaft of claim 1, wherein the longitudinal member is formed of monofilaments of a liquid crystal polymer.

5. A catheter comprising:
   a polymer inner layer; and
   a braid member disposed about the inner polymer layer;
   wherein the braid member includes at least one metallic member and at least one polymer member, the polymer member including a plurality of monofilaments arranged side by side to form a ribbon having two major faces and two minor faces, wherein the polymer member is twisted with respect to the inner polymer layer such that both major faces face the polymer layer at different points along a longitudinal axis of the catheter.

6. The catheter of claim 5, wherein the inner polymer layer defines a lumen, wherein the twisting of the polymer member causes a deformation of the inner polymer layer which affects the shape of the lumen.

7. The catheter of claim 6, wherein the twisting of the polymer member creates a ridge in the lumen.

8. The catheter of claim 6, further comprising a longitudinal member disposed between the braid member and the inner polymer member.

9. The catheter of claim 8, further comprising a tie layer disposed about the inner polymer layer, wherein the tie layer comprises a urethane material for improving adhesion between the inner polymer layer and the braid member.

10. The catheter of claim 6, wherein the polymer member is twisted such that the deformation of the inner polymer layer reduces the force needed to move a guidewire within the lumen.

11. The catheter of claim 5, wherein the polymer member is twisted at random intervals.

12. The catheter of claim 5, wherein the polymer member is twisted at predetermined intervals.

13. The catheter of claim 12, wherein the predetermined interval corresponds to 7.5 inches along the longitudinal axis.

14. The catheter of claim 11, further comprising a polymer outer layer disposed about the braid member.

15. An elongate shaft for use in a catheter, the elongate shaft comprising:
   a polymer inner layer defining a lumen;
   a reinforcing layer disposed about the inner layer, the reinforcing layer including a braid of at least a first member and a second member, wherein the first member is formed into a ribbon having a first major face and a second major face, the first member being twisted with respect to the inner layer such that the first major face is directed toward the inner layer at a first location along the elongate shaft and the second major face is directed toward the inner layer at a second location along the elongate shaft to form a twist in the first element between the first location and the second location; and
   a polymer Outer layer disposed about the reinforcing layer;
   wherein the reinforcing layer is placed about the inner layer such that a ridge extends into the lumen at a location corresponding to the twist in the first member.

16. The elongate shaft of claim 15, wherein the first member is formed of a polymer, and the second member is formed of a metal.

17. The elongate shaft of claim 16, wherein the ridge is adapted to reduce the force required to create relative movement between a guidewire disposed within the lumen and the elongate shaft.

18. The elongate shaft of claim 15, further comprising a longitudinal member.

19. The elongate shaft of claim 18, wherein the longitudinal member is disposed between the outer layer and the inner layer.

20. The elongate shaft of claim 19, wherein the longitudinal member is formed of a ribbon of monofilaments of a liquid crystal polymer.

* * * * *

UNITED STATES PATENT AND TRADEMARK OFFICE
CERTIFICATE OF CORRECTION

PATENT NO. : 6,866,660 B2
DATED : March 15, 2005
INVENTOR(S) : Robert J. Garabedian et al.

It is certified that error appears in the above-identified patent and that said Letters Patent is hereby corrected as shown below:

Column 1,
Line 67, delete "stricture", and insert therefor -- structure --.

Signed and Sealed this

Thirty-first Day of May, 2005

JON W. DUDAS
*Director of the United States Patent and Trademark Office*